US012109055B2

(12) United States Patent
Zheng et al.

(10) Patent No.: US 12,109,055 B2
(45) Date of Patent: Oct. 8, 2024

(54) COMPUTED TOMOGRAPHY (CT) MACHINE SYSTEM AND STATE MONITORING METHOD

(71) Applicant: Siemens Healthcare GmbH, Erlangen (DE)

(72) Inventors: Jing Ming Zheng, Shanghai (CN); Wen Wen Sui, Shanghai (CN); Hong De Mu, Shanghai (CN)

(73) Assignee: Siemens Healthineers AG, Erlangen (DE)

( * ) Notice: Subject to any disclaimer, the term of this patent is extended or adjusted under 35 U.S.C. 154(b) by 352 days.

(21) Appl. No.: 17/540,291

(22) Filed: Dec. 2, 2021

(65) Prior Publication Data

US 2022/0167932 A1    Jun. 2, 2022

(30) Foreign Application Priority Data

Dec. 2, 2020 (CN) .......................... 202011389971.1

(51) Int. Cl.
*A61B 6/10*       (2006.01)
*A61B 6/00*       (2006.01)
(Continued)

(52) U.S. Cl.
CPC .............. *A61B 6/102* (2013.01); *A61B 6/035* (2013.01); *A61B 6/0407* (2013.01);
(Continued)

(58) Field of Classification Search
CPC . A61B 34/20; A61B 34/30; A61B 2034/2055; A61B 2090/363; A61B 6/032;
(Continued)

(56) References Cited

U.S. PATENT DOCUMENTS

| | | | |
|---|---|---|---|
| 2002/0065461 A1 | 5/2002 | Cosman | |
| 2010/0168562 A1* | 7/2010 | Zhao | A61B 34/30 600/426 |

(Continued)

FOREIGN PATENT DOCUMENTS

| | | |
|---|---|---|
| CN | 102809464 A | 12/2012 |
| CN | 104545969 A | 4/2015 |

(Continued)

*Primary Examiner* — Keith M Raymond
*Assistant Examiner* — Milton Truong
(74) *Attorney, Agent, or Firm* — Banner & Witcoff Ltd.

(57) ABSTRACT

A computed tomography (CT) machine system and a state monitoring method are described. The CT machine system comprises a drum-shaped component, a 3D camera, and a control system. The drum-shaped component comprises a cylindrical body, with the center of the cylindrical body being provided with a hollow portion which is rotationally symmetrical about the central axis of the cylindrical body, a rotating component disposed in the cylindrical body rotating about the central axis, a plurality of trigger marks arranged in the rotating component, and a window provided in the cylindrical body. The 3D camera generates image data that is transferred to the control system, from which the control system determines state data of the CT machine. The 3D camera captures an image of the trigger marks through the window to generate marked image data.

19 Claims, 8 Drawing Sheets

(51) Int. Cl.
*A61B 6/03* (2006.01)
*A61B 6/04* (2006.01)
*A61B 6/58* (2024.01)

(52) U.S. Cl.
CPC .............. *A61B 6/4447* (2013.01); *A61B 6/54* (2013.01); *A61B 6/586* (2013.01)

(58) Field of Classification Search
CPC ........... A61B 6/102; A61B 6/035; G01P 3/38; G01H 9/00
See application file for complete search history.

(56) References Cited

U.S. PATENT DOCUMENTS

| | | | |
|---|---|---|---|
| 2014/0275953 A1* | 9/2014 | Gregerson | A61B 6/4405 600/407 |
| 2015/0104092 A1 | 4/2015 | Flohr et al. | |
| 2016/0249984 A1 | 9/2016 | Janssen | |
| 2016/0299088 A1* | 10/2016 | Zoboyan | A61B 6/54 |
| 2017/0049529 A1 | 2/2017 | Hannemann et al. | |
| 2018/0133518 A1* | 5/2018 | Harper | A61N 5/1045 |
| 2018/0185113 A1* | 7/2018 | Gregerson | A61B 34/35 |
| 2019/0150878 A1* | 5/2019 | Smith | A61B 6/5205 |
| 2019/0321657 A1 | 10/2019 | Hale | |
| 2020/0078097 A1* | 3/2020 | Gregerson | B25J 9/1666 |
| 2020/0121267 A1 | 4/2020 | Deutschmann | |
| 2020/0205748 A1 | 7/2020 | Pautsch et al. | |
| 2020/0323496 A1 | 10/2020 | Eibenberger et al. | |
| 2021/0128082 A1* | 5/2021 | Cohen | A61B 6/463 |

FOREIGN PATENT DOCUMENTS

| | | |
|---|---|---|
| CN | 104812307 A | 7/2015 |
| CN | 106469253 A | 3/2017 |
| CN | 110248618 A | 9/2019 |
| CN | 110392247 A | 10/2019 |
| CN | 111374675 A | 7/2020 |
| WO | WO-2020209568 A1 * | 10/2020 |

* cited by examiner

US 12,109,055 B2

COMPUTED TOMOGRAPHY (CT) MACHINE SYSTEM AND STATE MONITORING METHOD

CROSS-REFERENCE TO RELATED APPLICATIONS

The present application claims the benefit of the filing date of China patent application no. CN 202011389971.1, filed on Dec. 2, 2020, the contents of which are incorporated herein by reference in their entirety.

TECHNICAL FIELD

The present disclosure relates to the field of computed tomography (CT) systems and, in particular, to a CT machine system and state monitoring method.

BACKGROUND

Computed tomography (CT) refers to the electronic computer X-ray tomography technique, and a CT machine or a CT scanner is a fully functional instrument for the probing of disease using this technique. A CT machine generally comprises a gantry, a drum-shaped component which is located on the gantry and can be tilted, and a rotating component mounted within the drum-shaped component.

Machine faults in the gantry of the CT machine will generate noise, reduce the image scanning quality, and shorten the service life of the machine. Therefore, effective and real-time monitoring of the CT machine and a patient is important for the machine and personal safety. Thus, it is necessary to monitor vibration of the CT machine in time during service thereof to achieve a fault diagnosis. However, even if an end cover, which is one of critical components, is removed, it is still difficult to detect the rotating component that rotates at a high speed. As a result, this is high-cost and is time- and labor-consuming.

On the other hand, during examination the patient may be out of sight of a doctor. A doctor's mis-operation, such as pressing a tilt button when the patient is still on an examination table, may cause a collision between the patient and the machine and cause injury to the patient. In these cases, it is necessary to implement real-time monitoring and stop the current operation to avoid the collision between the patient and the machine.

At present, effective monitoring measures are required for the CT machine and the patient, especially for the rotating component. When the rotating component remains stationary, a contact vibration sensor is usually used to perform performance test and prediction for the CT machine. However, this method is difficult to apply to monitor a rotating component.

As for a patient under examination, the state thereof is usually determined by human vision, and possible damage to the patient from the machine is avoided accordingly.

SUMMARY

The main purpose of the present disclosure is to provide a CT machine system to solve the problem in the prior art that it is not easy to effectively monitor states of a CT machine and a patient. The present disclosure further aims to provide a method for monitoring the state of a CT machine to solve the problem in the prior art that it is not easy to effectively monitor states of a CT machine and a patient.

In order to achieve the above purposes, according to one aspect of the present disclosure, a CT machine system is provided, which comprises a drum-shaped component, a 3D camera, and a control system, wherein the drum-shaped component comprises: a cylindrical body, with the center of the cylindrical body being provided with a hollow portion which is rotationally symmetrical about the central axis of the cylindrical body; a rotating component disposed in the cylindrical body, the rotating component rotating about the central axis, and a plurality of trigger marks being arranged in the rotating component; and a window provided in the cylindrical body; wherein the 3D camera captures an image to generate image data, the image data is transferred to the control system, and the control system determines state data of a CT machine according to the received image data; and wherein the 3D camera captures an image of trigger marks through the window to generate mark image data.

The concept of the present disclosure is to monitor the vibration of the rotating component of the CT machine by using a machine vision technique. Machine vision is the application of an image analysis technique in factory automation, which simulates the human visual ability by using an optical system, a 3D camera, and an image processing tool, makes corresponding decisions, and finally commands a specific device to execute the decisions. In simple terms, machine vision uses a machine to replace human eyes to take an observation, measurement, and determination. In general, a machine vision system architecture is mainly composed of two parts, including hardware and software. The hardware devices mainly include a light source system, a lens, a video camera, an image capture card, and a vision processor. The software comprises core algorithms, which include a traditional digital image processing algorithm and a deep-learning based image processing algorithm. The CT machine system according to the present disclosure comprises hardware and software necessary for implementing machine vision.

In this way, an image of trigger marks located in the rotating component is captured by means of the 3D camera, such that information that reflects a motion state of the rotating component can be obtained, and the obtained information is then processed by means of the control system, thereby achieving effective and reliable monitoring of the motion state of the rotating component. By means of providing the window, a worker can detect vibration of the rotating component without removing the end cover of the drum-shaped component, thereby simplifying the maintenance. In addition, the control system may be a control system of the CT machine itself, and may also be an external additional control system if desired. The trigger mark is a component that can be optically recognized by the 3D camera, and may be a fluorescent dot. Similarly, it is also conceivable to provide a light source for the trigger mark such that the image thereof can be better captured by the 3D camera.

Further, according to an embodiment of the present disclosure, the trigger marks are uniformly arranged in the rotating component around the central axis and at predetermined intervals, such that the 3D camera captures at least three trigger marks through the window.

In this way, the 3D camera can always capture the image of at least three trigger marks, such that at least three sets of data will be provided for the motion state of the rotating component at each point in time, thereby improving the accuracy of data processing.

Further, according to an embodiment of the present disclosure, the cylindrical body is provided with an annular disc-shaped end cover at an axial end side, the window is provided in the end cover, and the trigger marks are arranged in the end face of the rotating component facing the end cover.

In this way, the cylindrical body itself is of an approximately annular in shape, and therefore the end cover matching thereto is also of an annular shape. The end cover is removable, and therefore the configuration in which the window is provided in the end cover and the trigger marks are arranged in the end face disposed opposite the end cover simplifies the installation and maintenance of the trigger marks. In this case, the 3D camera may be disposed on the side directly facing the end cover.

Further, according to an embodiment of the present disclosure, the rotating component comprises a peripheral rib portion which radially extends outwards, and the trigger marks are arranged in an edge region in an axial end face of the peripheral rib portion.

In this way, the trigger marks are uniformly arranged in the edge region, forming a circle. There are no other elements at the peripheral rib portion of the rotating component, such that providing trigger marks here will not affect the operation of other elements, and it is not necessary to redesign the layout of the elements. Furthermore, since the rotating component is a revolving body which has a relatively large linear velocity at the edge thereof, configuring the trigger marks in this region can reduce the requirement on the resolution of the 3D camera.

Further, according to an embodiment of the present disclosure, the window is of an elongated shape which extends perpendicular to a central horizontal plane where the central axis is located and is symmetrical about the central horizontal plane.

The elongated shape should be understood as a shape in which the longitudinal extension thereof is greater than the transverse extension. Here, the elongated shape may be a rectangle with rounded corners. In this way, in general the drum-shaped component will be tilted together with a gantry, i.e. rotate forward or backward around the diameter in the horizontal plane, and in this case the trigger marks adjacent to the axis of rotation have relatively small displacement, which has minimum affection on the image capture of the 3D camera.

Further, according to an embodiment of the present disclosure, the 3D camera is located on one side of the end cover, and a line connecting the 3D camera and the center of the window is parallel to the central axis.

In this way, the 3D camera is located in the central horizontal plane where the axis of rotation is located, and the projection of the 3D camera on the end cover falls on the midpoint of the window, which simplifies the relative positional relationship between the 3D camera and the trigger marks to simplifies the subsequent data processing and minimizes the desired size of the window, and prevents interference with a rotational component.

Further, according to an embodiment of the present disclosure, the window comprises a lens structure which allows the 3D camera to focus on the trigger marks.

In this way, the lens structure enables the 3D camera to always capture the image of the trigger marks without interference from other images.

Further, according to an embodiment of the present disclosure, the field of view of the 3D camera covers the entire end cover, and the 3D camera captures an image of a patient on an examination table to generate patient image data.

The 3D camera can not only capture a plane image, but also collect depth information of a photographed subject, i.e., the three-dimensional position, size, etc. According to the present disclosure, common 3D cameras can all be used in the present disclosure, and there is no special requirement for the imaging principle thereof, and the 3D camera should be understood as including necessary accessories required for the functions thereof. In addition to the trigger mark, the 3D camera further captures the image of the patient, and in this way, image data of the patient can be obtained for further processing.

Further, according to an embodiment of the present disclosure, the drum-shaped component can be tilted at a tilt angle relative to the horizontal direction, and the 3D camera captures an image of the drum-shaped component to generate tilt angle image data.

In this way, the system according to the present disclosure can also be used for monitoring a tilting state of the CT machine.

Further, according to an embodiment of the present disclosure, the control system comprises: a vibration determination module for determining a vibration state of the rotating component according to the mark image data; a tilt angle determination module for determining the tilt angle of the drum-shaped component according to the tilt angle image data; and a patient determination module for determining a contour and a position of the patient according to the patient image data.

In this way, by means of providing various determination modules in the control system and using the determination modules to respectively process the image data received from the 3D camera, the corresponding state data of interest can be determined.

Further, according to an embodiment of the present disclosure, the control system further comprises: a communication module for sending and receiving an operation instruction; and a fault diagnosis and alarm module for diagnosing whether there is a fault according to the vibration state, determining a distance between the patient and the drum-shaped component according to the tilt angle, the contour, and the position, and giving an alarm when the distance is less than a preset safety threshold.

The control system receives data from the outside by using the communication module, and transmits a generated operation instruction to other components. In this way, the control system can monitor the state of the CT machine according to the data obtained by the 3D camera, thereby improving the safety.

Here, the 3D camera generates, for example, point cloud data of a monitored subject. When the point cloud data is used for image analysis, a gray threshold segmentation method may be used for identifying the situation of illumination on the examining bed, and then the influence of illumination is eliminated accordingly; a gray centroid method is used for matching and division of virtual coordinates of the captured image with the coordinates defined in the design, so as to obtain the centroid of the trigger marks; and a gray weighing and weighted average method is used to obtain the reliable distances and vibrations of intersection points of the captured trigger marks.

According to another aspect of the present disclosure, a method for monitoring a state of a CT machine system is provided, with the CT machine system being implemented according to the CT machine system of the aforementioned embodiment, the method comprising: capturing an image of trigger marks located in a rotating component by means of a 3D camera to generate mark image data; processing the mark image data to obtain a mark displacement amount; and determining a vibration state of the rotating component according to the mark displacement amount.

In this way, the vibration state of the rotating component can be determined by means of capturing the image of the trigger marks that can reflect the motion state of the rotating component.

Further, according to an embodiment of the present disclosure, processing the mark image data to obtain a mark displacement amount comprises: generating three-dimensional coordinates of the trigger marks according to the mark image data; converting the three-dimensional coordinates to the horizontal plane to obtain two-dimensional coordinates; obtaining the mark displacement amount according to the two-dimensional coordinates.

When the captured image of the trigger mark is processed, the position changes of the trigger marks in three directions, especially in the two mutually-perpendicular directions and the vertical direction in a plane, are determined so as to determine the vibration state. Since the distances between three captured trigger points are relatively small, the displacement in the vertical direction is linearly converted to the coordinate system of the horizontal plane so as to ensure that the vibrations used come from the same point. In this way, the accuracy of the data is improved.

Further, according to an embodiment of the present disclosure, determining a vibration state of the rotating component according to the mark displacement amount comprises: determining the amplitude and vibration frequency of the rotating component according to the mark displacement amount.

After the data is collected, a vibration displacement curve with respect to time can be made, and the data in a time domain is then converted to the data in a frequency domain by means of Fourier transformation, so as to obtain an amplitude-frequency curve, a vibration frequency, and amplitude data.

Further, according to an embodiment of the present disclosure, the method further comprises: recording the vibration state of the rotating component during normal operation as a standard vibration state; recording the vibration state of the rotating component in real time as a real-time vibration state; comparing the real-time vibration state with the standard vibration state to obtain a real-time vibration deviation; and giving an alarm when the real-time vibration deviation exceeds a predetermined threshold.

Generally, an abnormal vibration state will be generated when the rotating component is interfered or has a fault. In this way, by means of monitoring the vibration deviation, it is possible to know whether the rotating component is interfered or has a fault.

Further, according to an embodiment of the present disclosure, the method further comprises: capturing an image of a drum-shaped component, which can be tilted at a tilt angle relative to the horizontal plane, by means of the 3D camera to generate image data of the drum-shaped component; and determining the tilt angle and a contour of the drum-shaped component according to the image data of the drum-shaped component.

Further, according to an embodiment of the present disclosure, the tilt of the drum-shaped component is controlled at a target pose in the absence of a patient; the current tilt angle and the contour of the drum-shaped component are determined to obtain an actual pose of the drum-shaped component (100); a pose deviation between the target pose and the actual pose is determined; and the pose control is calibrated according to the pose deviation.

In general, the pose of the drum-shaped component can be set in the control system of the CT machine, and the control accuracy will inevitably decrease as the service time increases. In this way, the pose control preset in the control system can be calibrated with the actual pose, thereby improving the system accuracy and then improving the safety.

Further, according to an embodiment of the present disclosure, the method further comprises: capturing an image of a patient on an examination table by means of the 3D camera to generate patient image data; and determining a contour and a position of the patient according to the patient image data.

Further, according to an embodiment of the present disclosure, the method further comprises: calculating, upon receiving a command of tilting the drum-shaped component, a target component contour when the drum-shaped component reaches a target position; calculating the minimum distance between the target component contour and the contour of the patient; and giving an alarm when the minimum distance exceeds a predetermined safety distance.

In this way, by means of calculating the target position in advance and comparing the relative relationship between the target position and the current position of the patient, an alarm is given when a danger is predicted, which can avoid unnecessary operations and ensure the safety of the patient.

According to another aspect of the present disclosure, a storage medium is provided, characterized in that the storage medium comprises a stored program, and the device having the storage medium therein is controlled to perform the method according to the embodiments of the second aspect of the present disclosure when the program is running.

The technical solution of the present disclosure is applied by means of providing a CT machine system which comprises a 3D camera and a rotating component, with trigger marks being provided in the rotating component, the vibration state of the rotating component can be determined by means of capturing the image of the trigger marks by the 3D camera. In this way, the problem in the prior art that it is not easy to effectively monitor states of a CT machine and a patient is solved.

In the several embodiments provided by the present disclosure, it should be understood that the disclosed technical content may be implemented in other ways. The device embodiments described above are merely schematic. For example, the division of the units or modules is a logical function division, and in actual implementations there may be other division methods. For example, a plurality of units or modules or components may be combined or integrated into another system, or some features may be omitted or not implemented. In addition, the mutual coupling or direct coupling or communication connection shown or discussed may be an indirect coupling or communication connection through some interfaces, modules or units, and may be electrical or otherwise.

The units or modules described as separate components may or may not be physically separated, and the components displayed as units or modules may or may not be physical units or modules, i.e. the components may be located in one place, or may be distributed on multiple network units or modules. Some or all of the units or modules may be selected according to actual needs to achieve the purpose of the solution of the embodiment.

In addition, the functional units or modules in the embodiments of the present disclosure can be integrated into one processing unit or module, or the units or modules can be present separately and physically, or two or more units or modules can be integrated into one unit or module. The above integrated unit or module can be implemented in the form of hardware or in the form of a software functional unit or module.

The integrated unit, if implemented in the form of a software functional unit and used as an independent product, can be stored in a computer readable storage medium. Based on such understanding, the technical solution of the present disclosure, in essence or the contribution to the prior art, or part of the technical solution can be embodied in the form of a software product. The computer software product is stored in a storage medium, and comprises a plurality of instructions used to cause a computer device, which may be a personal computer, a server, a network device, etc., to perform all or some of steps in the method described in the embodiments of the present disclosure. Moreover, the aforementioned storage medium includes: a USB flash disk, a read-only memory (ROM), a random access memory (RAM), a mobile hard disk, a magnetic disk or optical disc or other various media capable of storing program codes.

BRIEF DESCRIPTION OF THE DRAWINGS/FIGURES

The drawings of the description that constitute part of the present disclosure are used to provide further understanding of the present disclosure, and the illustrative embodiment of the present disclosure and the description thereof are intended to explain the present disclosure and do not constitute improper limitation to the present disclosure. In the drawings.

Figure 1:
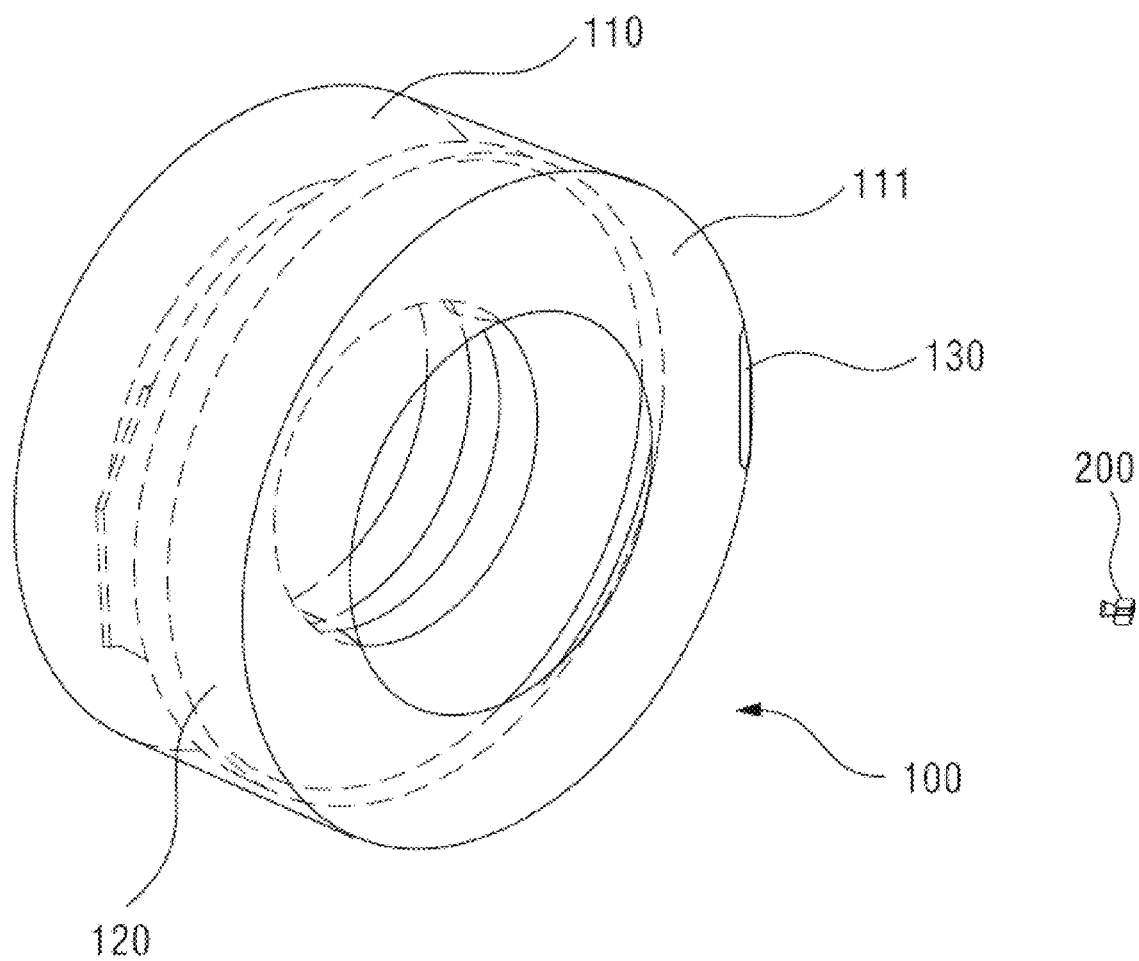
FIG. 1 shows a schematic diagram of an embodiment of a CT machine system according to the present disclosure.

In the above figures, the following reference numerals are included:
100: drum-shaped component;
110: cylindrical body;
111: end cover;
120: rotating component;
121: trigger mark;
130: window;
200: 3D camera;
300: control system;
310: vibration determination module;
320: tilt angle determination module;
330: patient contour and position determination module;
340: communication module;
350: fault diagnosis and alarm module;
F: field of view of 3D camera;
S: light receiving range;
A: vertical axis;
B: horizontal axis;
S100: method step;
S300: method step;
S500: method step;

DETAILED DESCRIPTION

In order to solve the problem in the prior art that it is not easy to effectively monitor states of a CT machine and a patient, a CT machine system is provided.

FIG. 1 shows a schematic diagram of an embodiment of the CT machine system according to the present disclosure. In FIG. 1, the CT machine system comprises a drum-shaped component 100, a 3D camera 200, and a control system 300 (not shown in detail). The drum-shaped component 100 comprises: a cylindrical body 110, with the center of the cylindrical body 110 being provided with a hollow portion which is rotationally symmetrical about the central axis of the cylindrical body 110; a rotating component 120 disposed in the cylindrical body 110, the rotating component 120 rotating about the central axis, and a plurality of trigger marks 121 (not shown in detail in FIG. 1) being arranged in the rotating component 120; and a window 130 provided in the cylindrical body 110. The 3D camera 200 captures an image to generate image data, the image data is transferred to the control system 300, and the control system 300 determines state data of the CT machine according to the received image data. The 3D camera 200 captures an image of the trigger marks 121 through the window 130 to generate mark image data.

In FIG. 1, the cylindrical body 110 has an annular disc-shaped end cover 111 at one axial end side, the window 130 is provided in the end cover 111, and the trigger marks 121 are arranged in the end face of the rotating component 120 facing the end cover 111. The cylindrical body 110 itself is of an approximately annular shape, and therefore the end cover 111 matching thereto is also of an annular shape. In this case, the 3D camera 120 is disposed on the side facing the end cover 111.

Figure 2:
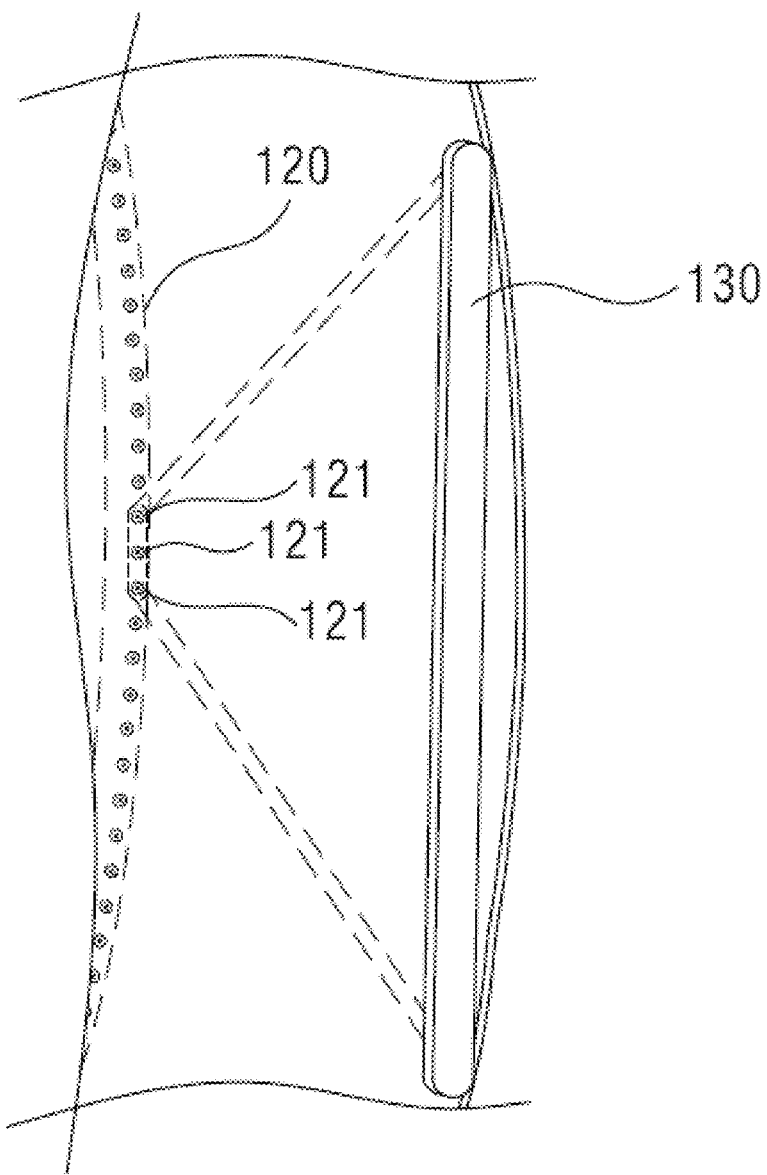
FIG. 2 shows a partial schematic diagram of the CT machine system according to the present disclosure.

FIG. 2 shows a partial schematic diagram of the CT machine system according to the present disclosure. In FIG. 2, the trigger marks 121 are uniformly arranged in the rotating component 120 around the central axis and at predetermined intervals such that the 3D camera 200 captures at least three trigger marks 121 through the window 130. The trigger marks 121 have small spacing, and are arranged in an edge region of the end face of the rotating component 120, forming a circle.

Preferably, the window 130 is of an elongated shape which extends perpendicular to a central horizontal plane where the central axis is located and is symmetrical about the central horizontal plane. The elongated shape can be understood as a shape in which the longitudinal extension thereof is greater than the transverse extension.

In this embodiment, the window 130 is of a substantially rectangular shape, with the long side thereof being a straight line, and the short side thereof being a circular arc, and having a certain thickness.

The window 130 may comprise a lens structure which allows the 3D camera 200 to focus on the trigger marks 121. The light path of the light that enters the window from the outside is indicated by a dashed line.

Figure 3A:
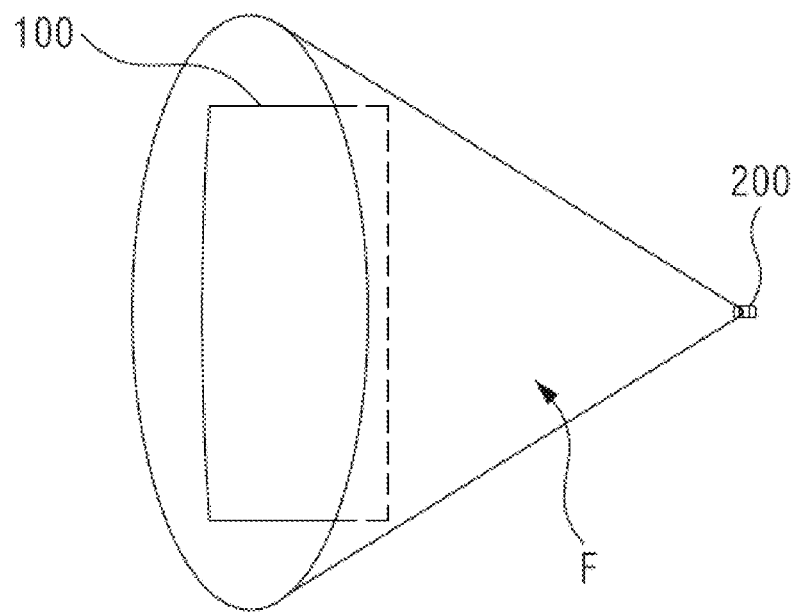
FIG. 3a shows a side view that illustrates the relationship between a drum-shaped component and the field of view of a 3D camera of the CT machine system according to the present disclosure.
Figure 3B:
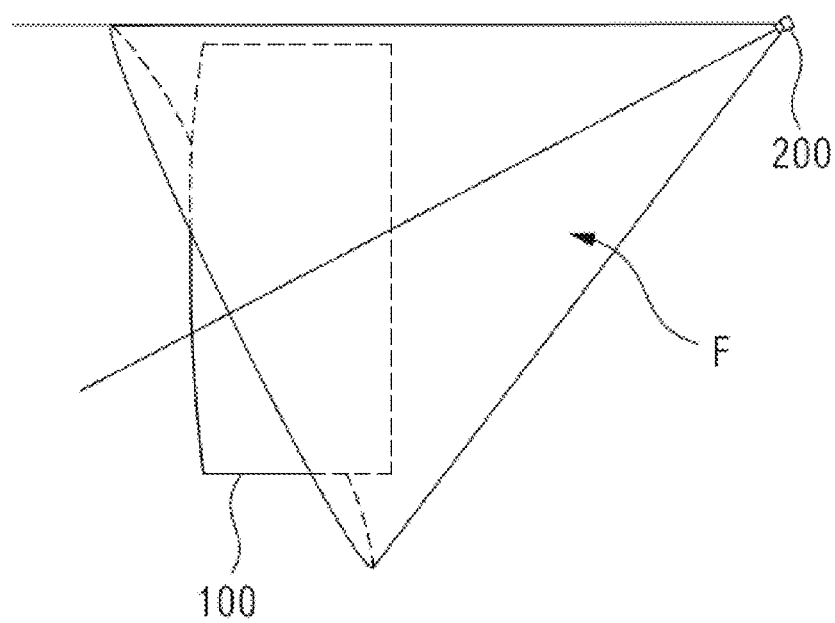
FIG. 3b shows a top view that illustrates the relationship between the drum-shaped component and the field of view of the 3D camera of the CT machine system according to the present disclosure.

FIGS. 3a and 3b show a side view and a top view, respectively, which illustrate the relationship between the drum-shaped component and the field of view of the 3D camera of the CT machine system according to the present disclosure. In the side view of FIG. 3a, the 3D camera 200 is located at the position of half height of the drum-shaped component 100, and the field of view F of the 3D camera 200 partially covers the drum-shaped component 100.

In the top view of FIG. 3b, the 3D camera 200 is located in the edge region directly facing the drum-shaped component 100, and in this case the field of view F covers most of the front surface of the drum-shaped component 100. By means of setting the position of the 3D camera 200 in the manner of this embodiment, it is possible to capture the complete contour of the front surface of the drum-shaped component 100 and also capture the contour of the part of interest of the patient.

Figure 4:
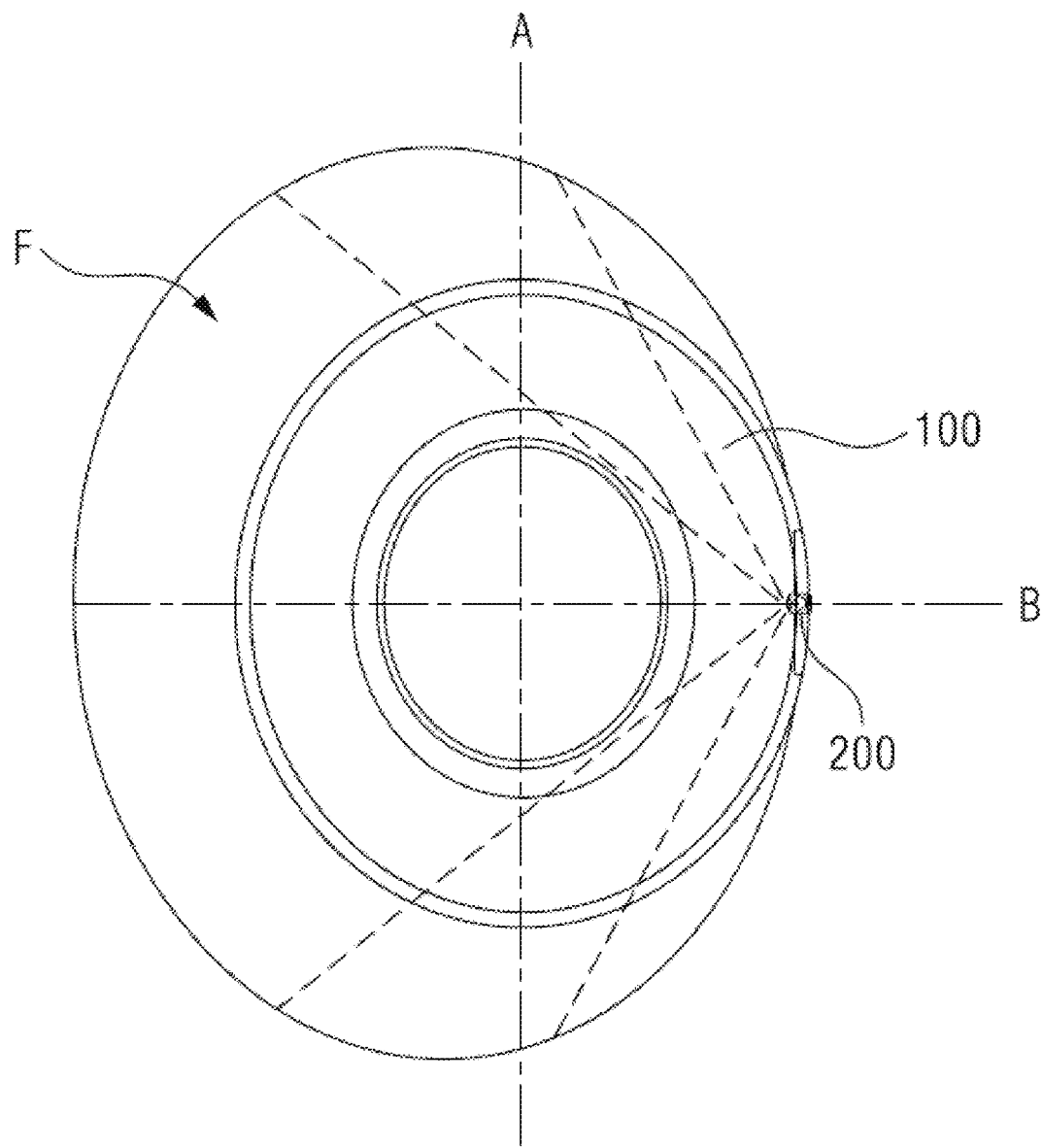
FIG. 4 shows a front view of the CT machine system according to the present disclosure.

FIG. 4 shows a front view of the CT machine system according to the present disclosure. In FIG. 4, the horizontal axis B and the vertical axis A of the drum-shaped component 100 are shown. The drum-shaped component 100 is tilted about the horizontal axis B, and it can be seen that the window 130 is symmetrical with respect to the horizontal plane, and the line connecting the 3D camera 200 and the center of the window 130 is perpendicular to the end cover 111, i.e. the 3D camera 200 is located in the central horizontal plane where the axis of rotation is located, and the projection of the 3D camera on the end cover falls on a midpoint of the window.

Figure 5:
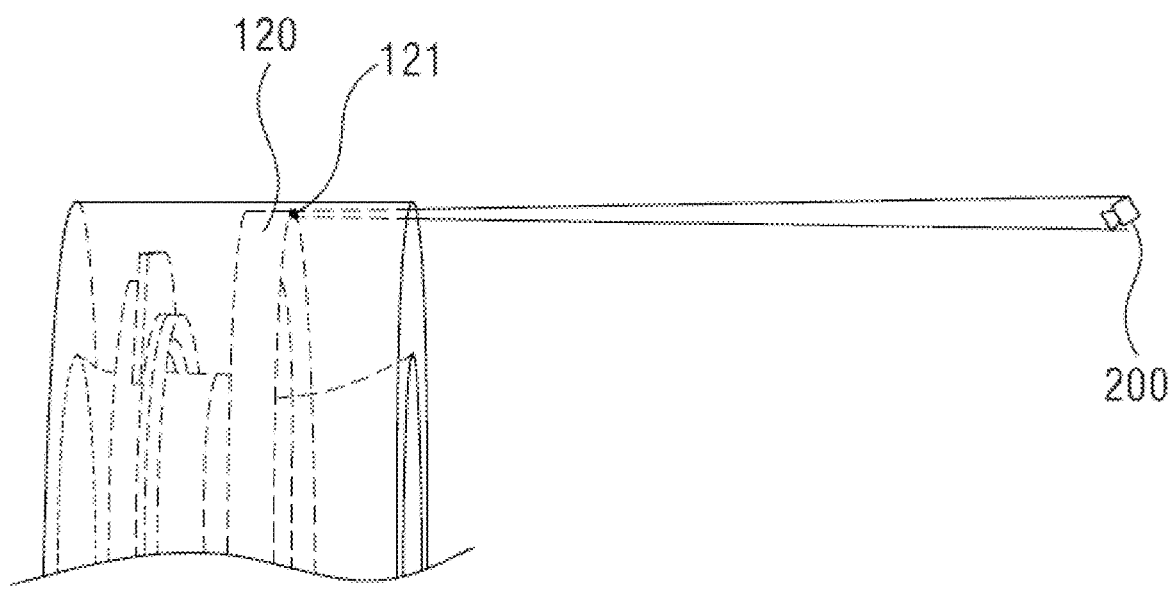
FIG. 5 shows a partial schematic diagram of the CT machine system according to the present disclosure.

FIG. 5 shows a partial schematic diagram of the CT machine system according to the present disclosure. In FIG. 5, a top view of the drum-shaped component 100 is shown. Various components are arranged in the drum-shaped component 100 and indicated by dashed lines. The rotating component 120 comprises a peripheral rib portion that radially extends outwards, and the trigger mark 121 is arranged in the edge region in the axial end face of the peripheral rib portion. The 3D camera 200 directly faces the end cover 111 and is on the same line as the window 130 and the trigger mark 121, and the line connecting the 3D camera 200 and the rotating component 120 represents an optical path for collecting information of the trigger mark 121. The optical path starts from the 3D camera 200, passes through the window 130, and reaches the trigger mark 121.

Figure 6A:
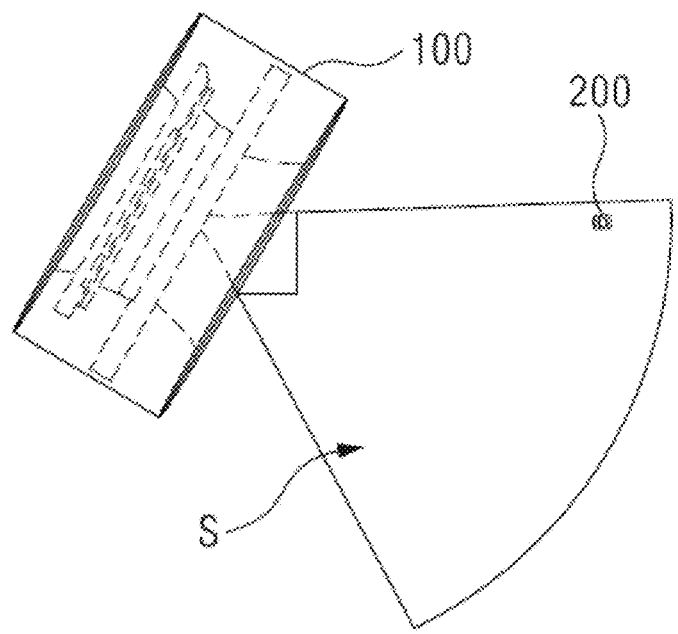
FIG. 6a shows a side view that illustrates the relationship between the drum-shaped component at the maximum forward tilt position and the field of view of the 3D camera according to the present disclosure.
Figure 6B:
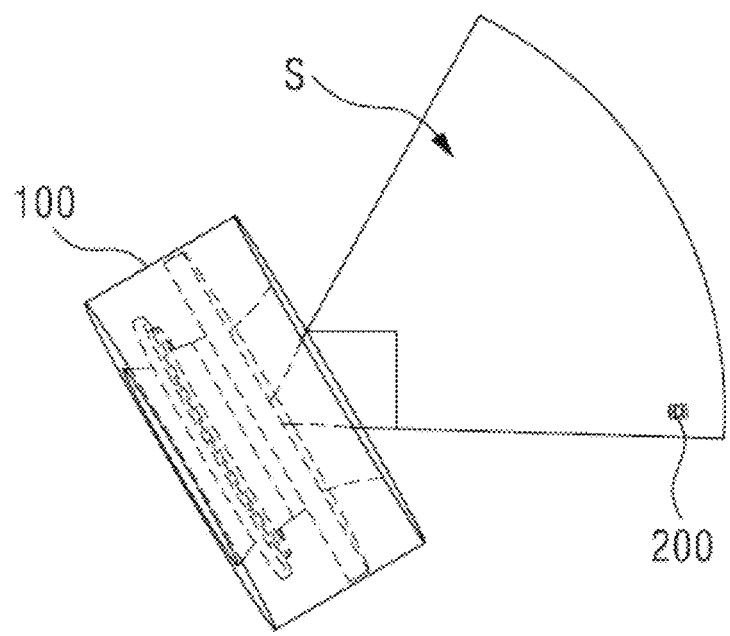
FIG. 6b shows a side view that illustrates the relationship between the drum-shaped component at the maximum backward tilt position and the field of view of the 3D camera according to the present disclosure.

FIGS. 6a and 6b respectively show a side view that illustrates the relationship between the drum-shaped component at the maximum forward tilt position and at the maximum backward tilt position and the field of view of the 3D camera. The drum-shaped component 100 can be tilted at a tilt angle relative to the horizontal direction, and the 3D camera 200 captures an image of the drum-shaped component 100 to generate tilt angle image data.

FIG. 6a shows a light receiving range S of the trigger mark 121 when the drum-shaped component 100 is tilted forward, and FIG. 6b shows the light receiving range S of the trigger mark 121 when the drum-shaped component 100 is tilted forward. In order to enable the 3D camera 200 to effectively capture an image of the trigger mark 121 when the drum-shaped component 100 is tilted, it can be seen from the figures that the window 130 has a suitable size and a lens structure such that the 3D camera 200 is always in the light receiving range S at all times.

In summary, FIGS. 3a, 3b, 4, 5, 6a, and 6b illustrate the positional relationship of the 3D camera 200 with the drum-shaped component 100, the window 130, and the trigger mark 121.

The field of view of the 3D camera 200 may cover the entire end cover 111, and the 3D camera 200 captures an image of a patient on an examination table to generate patient image data.

The 3D camera may not only capture a plane image, but may also collect depth information of a photographed subject, i.e., the three-dimensional position, size, etc. According to the present disclosure, common 3D cameras can all be implemented for this purpose, and there is no special requirement for the imaging principle thereof, and the 3D camera should be understood as including necessary accessories required for the functions thereof. In addition to the trigger mark, the 3D camera further captures the image of the patient, and in this way image data of the patient can be obtained for further processing.

In this way, the system according to the present disclosure can also be used for monitoring a tilting state of the CT machine.

Figure 7:
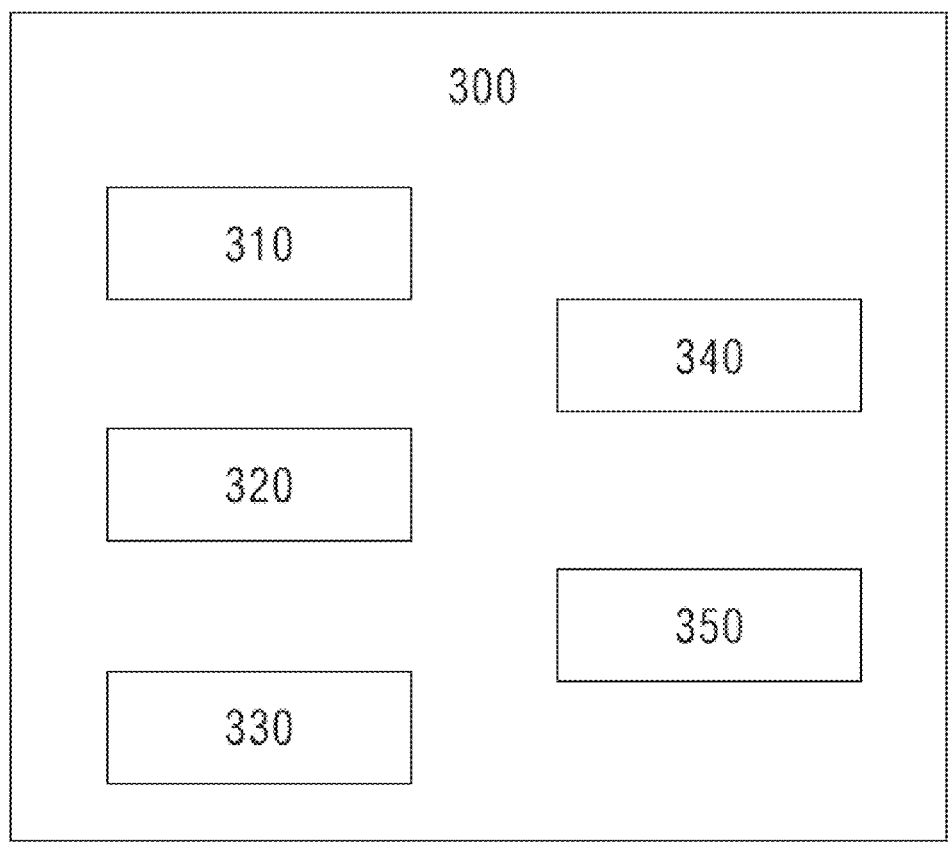
FIG. 7 shows a schematic diagram of a control system of the CT machine system according to the present disclosure.

FIG. 7 shows a schematic diagram of a control system 300 of the CT machine system according to the present disclosure. The control system comprises: a vibration determination module 310 for determining a vibration state of the rotating component 120 according to the mark image data; a tilt angle determination module 320 for determining a tilt angle of the drum-shaped component 100 according to the tilt angle image data; and a patient contour and position determination module 330 for determining a contour and a position of the patient according to the patient image data.

In addition, the control system further comprises: a communication module 340 for sending and receiving an operation instruction; and a fault diagnosis and alarm module 350 for diagnosing whether there is a fault or not according to the vibration state, determining a distance between the patient and the drum-shaped component 100 according to the tilt angle, the contour and the position, and giving an alarm when the distance is less than a preset safety threshold. The various modules as noted herein may be implemented as any suitable combination of processors, processing circuity, hardware components, and/or software implemented via execution of instructions by the processors, processing circuity, hardware components, etc.

Figure 8:
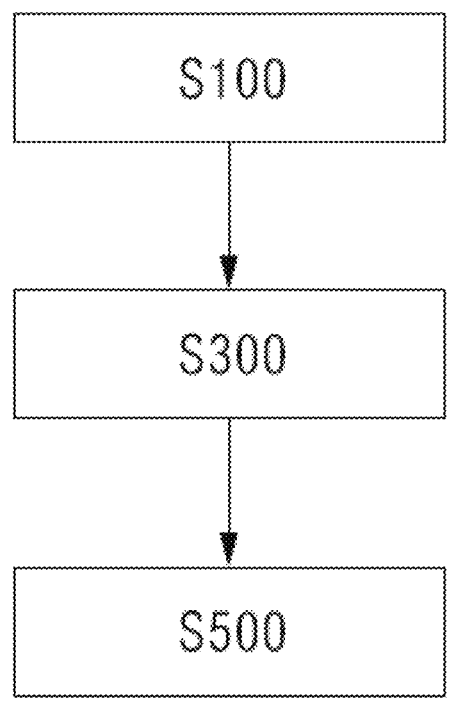
FIG. 8 shows a flow diagram of a state monitoring method according to the present disclosure.

FIG. 8 shows a flow diagram of a state monitoring method according to the present disclosure. A method for monitoring a state of a CT machine system is provided, the method comprising:

S100: capturing an image of trigger marks located in a rotating component by means of a 3D camera to generate mark image data;

S300: processing the mark image data to obtain a mark displacement amount; and

S500: determining a vibration state of the rotating component according to the mark displacement amount.

In this way, the vibration state of the rotating component can be determined by means of capturing the image of the trigger marks that can reflect the motion state of the rotating component.

Processing the mark image data to obtain a mark displacement amount may comprise: generating three-dimensional coordinates of the trigger marks according to the mark image data; converting the three-dimensional coordinates to the horizontal plane to obtain two-dimensional coordinates; obtaining the mark displacement amount according to the two-dimensional coordinates.

Determining a vibration state of the rotating component according to the mark displacement amount may comprise: determining the amplitude and vibration frequency of the rotating component according to the mark displacement amount. After the data is collected, a vibration displacement curve with respect to time can be made, and the data in a time domain is then converted to the data in a frequency domain by means of Fourier transformation, so as to obtain an amplitude-frequency curve, a vibration frequency and amplitude data.

The method may further comprise: recording the vibration state of the rotating component during normal operation as a standard vibration state; recording the vibration state of the rotating component in real time as a real-time vibration state; comparing the real-time vibration state with the standard vibration state to obtain a real-time vibration deviation; and giving an alarm when the real-time vibration deviation exceeds a predetermined threshold.

The method may further comprise: capturing an image of a drum-shaped component 100, which can be tilted at a tilt angle relative to the horizontal plane, by means of the 3D camera to generate image data of the drum-shaped component; and determining the tilt angle and a contour of the drum-shaped component 100 according to the image data of the drum-shaped component.

The tilt of the drum-shaped component 100 may be controlled at a target pose in the absence of a patient; the current tilt angle and the contour of the drum-shaped component 100 are determined to obtain an actual pose of the drum-shaped component 100; a pose deviation between the target pose and the actual pose is determined; and the pose control is calibrated according to the pose deviation.

The method may further comprise: capturing an image of a patient on an examination table by means of the 3D camera to generate patient image data; determining a contour and a position of the patient according to the patient image data.

The method may further comprise: calculating, upon receiving a command for tilting the drum-shaped component 100, a target component contour when the drum-shaped component 100 reaches a target position; calculating the minimum distance between the target component contour and the contour of the patient; and giving an alarm when the minimum distance exceeds a predetermined safety distance.

The present disclosure is implemented herein using various examples, by means of providing a CT machine system which comprises a 3D camera and a rotating component, with trigger marks being provided in the rotating component, the vibration state of the rotating component can be determined by means of capturing the image of the trigger marks by the 3D camera. In this way, the problem in the prior art that it is not easy to effectively monitor states of a CT machine and a patient is solved.

From the above description, it can be seen that the above-mentioned embodiments of the present disclosure achieve the following technical effects:

1. An abnormal condition within the CT machine can be detected when it first occurs, thereby further avoiding damage. In addition, collisions between the patient and the CT machine are avoided. Therefore, the CT performance is maintained in a reliable state, thereby ensuring the safety of the machine and the patient.

2. The system achieves the monitoring of vibration and the state monitoring for preventing collisions between the patient and the machine by only use of a simple 3D camera. The 3D camera used is much cheaper than a contact vibration sensor commonly used in vibration testing. Therefore, the method saves costs.

3. Also, the state monitoring of collisions between the CT machine and the patient is achieved in an unmanned and non-contact manner. The state of the CT gantry is monitored in real time, which provides the feasibility of analysis on the internal abnormal condition, so it is not necessary to remove the CT gantry and detect a high-speed rotating component. Therefore, the method is time-saving and labor-saving.

It should be noted that the embodiments in the present disclosure and the features in the embodiments can be combined with each other without conflict. The present disclosure will be described in detail below with reference to the accompanying drawings and the embodiments.

It should also be noted that all the technical and scientific terms used herein have the same meaning as commonly understood by those of ordinary skill in the art to which the present disclosure belongs, unless otherwise indicated.

In the present disclosure, if there is no explanation to the contrary, the orientation words used such as "upper", "lower", "top" and "bottom" usually refer to the directions shown in the drawings, or refer to a component itself in the vertical, perpendicular or gravitational direction. Similarly, for ease of understanding and description, the orientation words "inside" and "outside" refer to the inside and the outside relative to the contour of the component itself, but the above orientation terms are not intended to limit the present disclosure.

The embodiments described above are merely some of rather than all of the embodiments of the present disclosure. On the basis of the embodiments of the present disclosure, all other embodiments which would have been obtained by those of ordinary skill in the art without involving any inventive effort shall fall within the scope of protection of the present disclosure.

It should be noted that the terminology used herein is merely for description of specific embodiments and is not intended to limit the exemplary embodiments according to the present disclosure. As used herein, the singular forms are also intended to include the plural forms, unless the context clearly indicates otherwise. In addition, it should also be understood that when the term "including" and/or "comprising" is used in this specification, it indicates the presence of features, steps, operations, devices, components, and/or combinations thereof.

It should be noted that the terms such as "first" and "second" in the description and the claims of the present disclosure and in the aforementioned accompanying drawings are used to distinguish similar objects, and do not necessarily describe a specific order of precedence. It should be understood that the data used in this way can be interchanged where appropriate, so that the embodiments of the present disclosure described herein can be implemented in a sequence other than those illustrated or described herein.

The aforementioned description is merely illustrative of the preferred embodiments of the present disclosure and is not intended to limit the present disclosure, and various changes and modifications would have been made by a person skilled in the art. Any modifications, equivalent substitutions, improvements, etc. made within the spirit and principles of the present disclosure shall fall within the scope of protection of the present disclosure.

What is claimed is:

1. A computed tomography (CT) machine system, comprising:
a three-dimensional (3D) camera;

a computing device; and
a drum-shaped component including (i) a cylindrical body including a window, the cylindrical body being identified with a central axis, and the center of the cylindrical body being provided with a hollow portion which is rotationally symmetric about the central axis, and (ii) a rotating component disposed in the cylindrical body, the rotating component being rotatable about the central axis,
wherein the rotating component comprises an arrangement of a plurality of trigger marks,
wherein the 3D camera is configured to capture, through the window, an image of the plurality of trigger marks that are arranged in the rotating component to generate image data that is transferred to the computing device,
wherein the window comprises a lens structure that enables the 3D camera to focus on the plurality of trigger marks, and
wherein the computing device is configured to determine state data of the CT machine based upon the transferred image data.

2. The CT machine system of claim 1, wherein the plurality of trigger marks are uniformly arranged in the rotating component around the central axis such that the 3D camera captures an image of at least three of the plurality of trigger marks through the window.

3. The CT machine system of claim 1, wherein the cylindrical body includes an annular disc-shaped end cover at an axial end side, and
wherein the window is provided in the annular disc-shaped end cover.

4. The CT machine system of claim 1, wherein the rotating component comprises a peripheral rib portion that extends radially outwards, and
wherein the plurality of trigger marks are arranged in an axial end face of the peripheral rib portion.

5. The CT machine system of claim 1, wherein the window is of an elongated shape that extends perpendicular to a central horizontal plane where the central axis of the cylindrical body is located and is symmetrical about the central horizontal plane.

6. The CT machine system of claim 3, wherein the 3D camera is located on one side of the annular disc-shaped end cover.

7. The CT machine system of claim 3, wherein:
a field of view of the 3D camera covers an entirety of the annular disc-shaped end cover,
the drum-shaped component is tiltable, and
the 3D camera is configured to capture an image of the drum-shaped component to generate tilt angle image data.

8. The CT machine system of claim 7, wherein the 3D camera is further configured to capture an image of a patient on an examination table to generate patient image data, and
wherein the computing device comprises:
vibration determination circuitry configured to determine a vibration state of the rotating component based upon the image data;
tilt angle determination circuitry configured to determine a tilt angle of the drum-shaped component based upon the tilt angle image data; and
patient contour and position determination circuitry configured to determine a contour of the patient and a position of the patient based upon the patient image data.

9. The CT machine system of claim 8, wherein the computing device further comprises:
fault diagnosis and alarm circuitry configured to diagnose whether there is a fault based upon the vibration state and to determine a distance between the patient and the drum-shaped component based upon the tilt angle, the contour of the patient, and the position of the patient.

10. A method for monitoring a state of a computed tomography (CT) machine system, comprising:
operating the CT machine system comprising a drum-shaped component including (i) a cylindrical body including a window, the cylindrical body being identified with a central axis, and the center of the cylindrical body being provided with a hollow portion which is rotationally symmetric about the central axis, and (i) a rotating component disposed in the cylindrical body,
rotating, during operation of the CT machine system, the rotating component about the central axis, the rotating component comprising an arrangement of a plurality of trigger marks,
capturing, via a three-dimensional (3D) camera through the window, an image of the plurality of trigger marks that are arranged in the rotating component to generate image data,
wherein the window comprises a lens structure that enables the 3D camera to focus on the plurality of trigger marks;
transferring the image data to processing circuitry;
processing, via the processing circuitry, the image data to calculate a mark displacement distance;
determining, via the processing circuitry, a vibration state of the rotating component based upon the mark displacement distance.

11. The method of claim 10, further comprising:
generating 3D coordinates of the plurality of trigger marks based upon the image data;
converting the 3D coordinates to a first plane to obtain two-dimensional (2D) coordinates;
calculating the mark displacement distance based upon the 2D coordinates; and
determining an amplitude and vibration frequency of the rotating component based upon the mark displacement distance.

12. The method of claim 10, further comprising:
recording the vibration state of the rotating component during operation as a first vibration state;
recording the vibration state of the rotating component during operation as a second vibration state;
comparing the second vibration state with the first vibration state to obtain a vibration deviation; and
generating an alarm when the vibration deviation exceeds a predetermined deviation value threshold.

13. The method of claim 10, further comprising:
capturing, via the 3D camera, an image of the drum-shaped component of the CT machine system, which is tiltable at a tilt angle relative to a first plane, to generate the image data including the drum-shaped component;
determining the tilt angle of the drum-shaped component and a contour of the drum-shaped component based upon the image data;
causing the drum-shaped component to tilt at a target pose in the absence of a patient;
determining a tilt angle and a contour of the drum-shaped component to obtain an actual pose of the drum-shaped component;
determining a pose deviation between the target pose and the actual pose; and
performing a pose calibration based upon the pose deviation.

14. The method of claim 10, further comprising:
capturing, via the 3D camera, an image of a patient on an examination table to generate patient image data;
determining a contour of the patient and a position of the patient based upon the patient image data;
calculating, upon receiving a command to tilt a drum-shaped component of the CT machine system, a target component contour when the drum-shaped component reaches a target position;
calculating a distance between the target component contour and the contour of the patient; and
generating an alarm when the distance exceeds a predetermined distance threshold.

15. The CT machine system of claim 3, wherein the plurality of trigger marks are arranged in an end face of the rotating component facing the annular disc-shaped end cover.

16. The CT machine system of claim 6, wherein a line connecting the 3D camera and a center of the window is parallel to the central axis of the cylindrical body.

17. The CT machine system of claim 9, wherein the fault diagnosis and alarm circuitry is further configured to provide an alarm when the distance between the patient and the drum-shaped component is less than a predetermined threshold distance.

18. The CT machine system of claim 3, wherein a field of view of the 3D camera covers an entirety of the annular disc-shaped end cover.

19. The CT machine system of claim 1, wherein a field of view of the 3D camera enables an entire contour of a surface of the drum-shaped component and a contour of a part of interest of a patient on an examination table of the CT machine system to be concurrently captured.

* * * * *